United States Patent
Greener

(10) Patent No.: US 9,751,833 B2
(45) Date of Patent: Sep. 5, 2017

(54) ANTIMICROBIAL BIGUANIDE METAL COMPLEXES

(75) Inventor: Bryan Greener, Elvington (GB)

(73) Assignee: Smith & Nephew PLC, London (GB)

(*) Notice: Subject to any disclaimer, the term of this patent is extended or adjusted under 35 U.S.C. 154(b) by 771 days.

(21) Appl. No.: 11/922,894

(22) PCT Filed: Jun. 27, 2006

(86) PCT No.: PCT/GB2006/002364
§ 371 (c)(1),
(2), (4) Date: May 21, 2008

(87) PCT Pub. No.: WO2007/000590
PCT Pub. Date: Jan. 4, 2007

(65) Prior Publication Data
US 2009/0123513 A1     May 14, 2009

(30) Foreign Application Priority Data

Jun. 27, 2005 (GB) .................................. 0512916.8
Jun. 27, 2005 (GB) .................................. 0513127.1

(51) Int. Cl.
*C07C 279/26* (2006.01)
*A01N 59/16* (2006.01)

(52) U.S. Cl.
CPC .......... *C07C 279/265* (2013.01); *A01N 59/16* (2013.01); *C07C 279/26* (2013.01)

(58) Field of Classification Search
CPC .... C07C 279/265; C07C 279/26; A01N 59/16
See application file for complete search history.

(56) References Cited

U.S. PATENT DOCUMENTS

| | | | |
|---|---|---|---|
| 2,510,510 | A | 6/1950 | Mendenhall |
| 3,004,824 | A | 10/1961 | John |
| 3,130,002 | A | 4/1964 | Fuchs |
| 3,432,428 | A | 3/1969 | Wirth, Jr. et al. |
| 3,468,898 | A | 9/1969 | Cutler et al. |
| 3,702,298 | A | 11/1972 | Zsoldos, Jr. et al. |
| 4,123,248 | A | 10/1978 | Drake |
| 4,181,786 | A | 1/1980 | Mune et al. |
| 4,515,772 | A | 5/1985 | Parran, Jr. et al. |
| 4,822,512 | A | 4/1989 | Auchincloss |
| 4,875,475 | A | 10/1989 | Comte et al. |
| 5,151,122 | A | 9/1992 | Atsumi et al. |
| 5,223,149 | A * | 6/1993 | Antelman ............ 210/764 |
| 5,266,534 | A | 11/1993 | Atsumi et al. |
| 5,395,651 | A | 3/1995 | Sodervall et al. |
| 5,470,585 | A | 11/1995 | Gilchrist |
| 5,837,275 | A | 11/1998 | Burrell et al. |
| 6,264,936 | B1 * | 7/2001 | Sawan et al. ............ 424/78.26 |
| 6,365,130 | B1 | 4/2002 | Barry et al. |
| 2001/0043951 | A1 | 11/2001 | Kim et al. |
| 2002/0192298 | A1 | 12/2002 | Burrell et al. |
| 2003/0049300 | A1 | 3/2003 | Terry |
| 2003/0059456 | A1 | 3/2003 | Malcolm et al. |
| 2003/0072810 | A1 | 4/2003 | Burrell et al. |
| 2004/0002444 | A1 | 1/2004 | Shiba |
| 2004/0091603 | A1 | 5/2004 | Priewe |
| 2004/0215204 | A1 | 10/2004 | Davison et al. |
| 2005/0026802 | A1 | 2/2005 | Kilkenny et al. |
| 2006/0051385 | A1 | 3/2006 | Scholz |
| 2006/0148958 | A1 | 7/2006 | Haraguchi et al. |
| 2006/0177517 | A1 | 8/2006 | Shiba |
| 2009/0110750 | A1 | 4/2009 | Greener |
| 2009/0238850 | A1 | 9/2009 | Greener |
| 2009/0291821 | A1 | 11/2009 | Gard |

FOREIGN PATENT DOCUMENTS

| | | |
|---|---|---|
| CA | 2371328 | 1/2001 |
| CN | 1434729 | 6/2003 |
| CN | 1536986 | 10/2004 |
| DE | 85 33 134 U1 | 4/1986 |
| EP | 0 073 455 A2 | 3/1983 |
| EP | 0298726 A1 | 1/1989 |
| EP | 0 328 421 A | 8/1989 |
| EP | 328421 A2 * | 8/1989 |
| EP | 0 528 191 | 2/1993 |
| EP | 1159972 B1 | 12/2001 |
| EP | 1 304 082 A | 4/2003 |
| EP | 1 350 479 A | 10/2003 |
| FR | 2755612 A | 5/1998 |

(Continued)

OTHER PUBLICATIONS

International Search Report dated Jul. 23, 2007 in related Application No. PCT/GB2006/000279.
Sarangi, et al., 'Studies on Local Anaesthetics,' *The Indian Journal of Pharmacy*, 35(3):96-97 (Aug. 26, 2009).
Chatterjee, et al., 'Unusual oxidation states of silver: silver(III) complexation to 1-amidino-o-alkylpseudourea, piperazinedibiguanide, and related ligands,' *Journal of the Indian Chemical Society*, Calcutta, In, 47(10):1021-1022 (1970).
Das, 'Kinetics of oxidation of glyoxylic acid by [ethylenebis(biguanide)] silver(III) in aqueous media,' *Polyhedron*, 23:895-901 (2004).
Ray, 'Complex compounds of biguanides and guanylureas with metallic elements,' *Chemical Reviews*, 61:313-359 (1961).
Ray, 'An EPR study of some Copper(II) coordination compounds of substituted biguanides, Part IV,' *Inorganica Chimica Acta*, 174:257-262 (1990) Abstract.
Sweeney, et al., 'Antidiabetic and Antimalanal Biguanide Drugs are Metal-Interactive Antiproteolytic Agents,' *Biochemical Pharmacology*, Pergamon, Oxford,GB, 66(4):663-677 (2003).

(Continued)

*Primary Examiner* — Sudhakar Katakam
(74) *Attorney, Agent, or Firm* — Kilpatrick, Townsend & Stockton LLP

(57) ABSTRACT

A compound comprising a metal species and a biologically acceptable ligand, wherein the biologically acceptable ligand comprises a biguanide moiety, and wherein the biologically acceptable ligand forms a complex with the metal species in which the metal species is stabilised in an oxidation state greater than 1+. Compositions and medical devices comprising the compound. A method for the treatment or prophylaxis of microbial, including bacterial, infections, comprising the use of such compounds, compositions or medical devices.

7 Claims, No Drawings

(56) References Cited

FOREIGN PATENT DOCUMENTS

| | | |
|---|---|---|
| JP | 64015054 | 1/1989 |
| JP | H217071 | 1/1990 |
| JP | 03002106 | 1/1991 |
| JP | 03090007 | 4/1991 |
| JP | 04 049208 A | 2/1992 |
| JP | 05124919 | 5/1993 |
| JP | 06511188 | 12/1994 |
| JP | 09110463 | 4/1997 |
| JP | 09505112 | 5/1997 |
| JP | 09510629 | 10/1997 |
| JP | 2001508041 | 5/1998 |
| JP | 11181109 | 7/1999 |
| JP | 2002524475 | 8/2002 |
| JP | 2003517463 | 5/2003 |
| JP | 200400543 | 1/2004 |
| JP | 2004508895 | 3/2004 |
| JP | 2004510794 | 4/2004 |
| JP | 2004517704 | 6/2004 |
| JP | 2005112735 | 4/2005 |
| JP | 2005514402 | 5/2005 |
| WO | 9513704 | 5/1995 |
| WO | 9818330 | 5/1998 |
| WO | 0009173 | 2/2000 |
| WO | 0015036 | 3/2000 |
| WO | WO 01/43788 | 6/2001 |
| WO | 0218003 A | 3/2002 |
| WO | 0224240 | 3/2002 |
| WO | 02062403 | 8/2002 |
| WO | 02076426 | 10/2002 |
| WO | 03055941 | 7/2003 |
| WO | 03094774 A | 11/2003 |
| WO | 2004024197 | 3/2004 |
| WO | 2004072138 | 8/2004 |
| WO | 2004075906 | 9/2004 |
| WO | 2006058906 | 6/2006 |
| WO | 2007000590 | 1/2007 |
| WO | WO 2007/000591 | 1/2007 |
| WO | WO 2007/085852 A2 | 8/2007 |
| WO | 2007142579 | 12/2007 |

OTHER PUBLICATIONS

Woo, et al., 'Vanadyl-Biguanide Complexes as Potential Synergistic Insulin Mimics,' *Journal of Inorganic Biochemistry*, New York, NY, 76(3/4):251-257 (1999).

Database WPI, Derwent Publications Ltd., London, GB; Aquatic organisms repellent for bottom ships, fishing nets, etc., & JP 04 049208 A (Sanwa Chem Co Ltd) (1992) Abstract.

'Relationship between tissue culture cytotoxicity and acute toxicity in mice of biguanide derivatives,' *Journal of Antibiotics*, Japan Antibiotics Research Association, Tokyo, Japan, 18(4):196-199 (1965).

International Search Report in related Application No. PCT/GB2006/002365.

Shirkhanzadeh, et al., "Bioactive delivery systems for the slow release of antibiotics: incorporation of $Ag^+$ ions into micro-porous hydroxyapatite coatings," *Materials Letters*, 1995, 24:7-12.

Office Action dated Jun. 27, 2011 in related Chinese Patent Application No. 200680031328.3 English translation Office Action dated Dec. 18, 2009 in related Chinese Patent Application No. 200680031328.3 English translation.

Miyasato, et al., "A newly developed woud dressing made of alginate fiber containing zeolite substituted by silver and zinc: Fundamental Study," *Japanese Phamacology & Therapeutics*, EMBASE, Jan. 1, 1999, vol. 17(4), pp. 677-683, 685-703.

International Search Report dated Oct. 12, 2006 in Application No. PCT/GB2006/002364.

IPRP dated Jan. 9, 2008 in Application No. PCT/GB2006/002365.

Office Action dated Dec. 7, 2011 in Chinese Patent Application No. 2006800314093.

Office Action dated Aug. 18, 2009 in European Patent Application No. 07705047.4.

Office Action dated Dec. 27, 2011 in Chinese Application No. 200780011603.

Office Action dated Mar. 22, 2011 in European Patent Application No. 07705047.4.

Takenaka, et al., "Efficacy of IntraSite Gel Conformable Dressing Type in Patients with Burn Ulcer," Medicine and Pharmacy, 52(5):827-834 (2004).

Ui, et al., "Clinical Studies for IntraSite Gel System on Various Wounds," Clinical Medication, 13(13):3507-3519 (1997).

A Thermal Burn, 26(2):63-71 (2000).

Lee, et al., "Antibacterial Mechanism of Long-Chain Polyphosphates in *Staphylococcus aureus*," Journal of Food Protection, 57(4):289-294 (1994).

Qin, "Silver Streak," Textile Horizons, Nov./Dec. 2004, pp. 16-17.

Monshipouri, et al., "Emulsification preparation of calcium alginate beads in the presence of sequesterant," J. Microencapsulation, 12(3):255-262 (1995).

Machida, et al., "Preparation of a Novel Patch for the Treatment of Deep Wounds and Evaluation of the Therapeutic Effect on Rats," Pharmaceutics, 57(1):57-63 (1997).

Suzuki, et al., "Development of New Hydrocolloid-type Wound Dressing Containing Silver Sulfadiazine," Pharmacology and Treatment, 28(7):621-633 (2000).

Notice of Reasons for Rejection dated Apr. 24, 2012 in related Japanese Patent Application No. 2008-517607.

Office Action dated Apr. 28, 2012 in related Chinese Patent Application No. 200680031328.3.

Horizon Chemical Co., Inc. Material Safety Data Sheet dated Jan. 21, 2004 (09 pages).

Westlake CA&O Material Safety Data Sheet dated Oct. 23, 1997 (08 pages).

Office Action dated Apr. 14, 2011 in related Australian Patent Application No. 2006263606.

Office Action dated Mar. 26, 2010 in related Chinese Patent Application No. 200680031409.3.

Office Action dated Dec. 7, 2011 in related Chinese Patent Application No. 2006800314093.

Office Action dated Nov. 1, 2011 in related Australian Application No. 2007209145.

Kim, et al., "Hydroxyapatite porous scaffold engineered with biological polymer hybrid coating for antibiotic Vancomycin release," *Journal of Materials Science: Materials in Medicine*, 16:189-195 (2005).

Office Action dated Dec. 20, 2011 in related Japanese Patent Application No. 2008-518960.

Office Action dated Sep. 11, 2012 in related Japanese Patent Application No. 2008-551878.

Office Action dated Mar. 11, 2013 in related Korean Patent Application No. 10-2008-7000719.

File No. STD/1081, "Silver sodium hydrogen zirconium phosphate", NICNAS Australia, (2004) accessed at http://www.nicnas.gov.au/publications/car/new/std/stdfullr/std1000fr/std1081fr.pdf, on Jan. 10, 2013.

Silver Oxide: retrieved from internet: http://en.wikipedia.org/wiki/Silver_oxide. Retrieved on Oct. 9, 2013.

New wiki-Silver Oxide: retrieved from internet: https://en.wikipedia.org/wiki/Silver_oxide. Retrieved on Sep. 17, 2015.

Silver oxide MSDS: retrieved from internet: http://www.saltlakemetals.com/MSDS_Silver_Oxide.htm. Retrieved on Sep. 17, 2015.

Silver Oxide, http://www.saltlakemetals.com/MSDS_Silver_Oxide.html. Retrieved on Dec. 28, 2016.

Australia Patent Application No. 2006263606, Office Action dated Apr. 14, 2011, 2 pages.

Bandyopadhyay et al., Kinetics of Oxidation of Azide by [Ethylenebis(biguanide)]silver(III) in Aqueous Acidic Media, European Journal of Inorganic Chemistry, vol. 2003, Issue 24, 2003, pp. 4308-4312.

Chinese Application No. 200680031309.3, Office Action mailed on Dec. 7, 2011.

(56) References Cited

OTHER PUBLICATIONS

Chinese Application No. 200680031328.3, Office Action mailed on Feb. 5, 2015, 15 pages.
Dasgupta et al., Decomposition kinetics of bis (biguanide) silver (III) cation in acid perchlorate media, Transition Metal Chemistry, vol. 14, Feb. 1989, pp. 19-21.
Japanese Application No. 2008-518960, Office Action mailed on Dec. 3, 2013, 16 pages.
Japanese Application No. 2015-031988, Office Action mailed on Jan. 10, 2017, 11 pages.
Linnert et al., Long-lived nonmetallic silver clusters in aqueous solution: preparation and photolysis, Journal of American chemical society, vol. 112, Issue 12, 1990, pp. 4657-4664.
Nunns et al., Inorganic block copolymer lithography, Polymer, vol. 54, 2013, pp. 1269-1284.
International Application No. PCT/GB2007/000279, International Search Report mailed on Apr. 8, 2009.

\* cited by examiner

ANTIMICROBIAL BIGUANIDE METAL COMPLEXES

This application is the U.S. national phase of International Application No. PCT/GB2006/002364 filed on Jun. 27, 2006 and published in English on Jan. 4, 2007 as International Publication No. WO 2007/000590 A1, which application claims priority to Great Britain Patent Application No. 0512916.8 filed on Jun. 27, 2005 and Great Britain Patent Application No. 0513127.1 filed on Jun. 27, 2005, the contents of which are incorporated herein by reference.

This invention relates to compositions comprising compounds for the treatment or prophylaxis of microbial, including bacterial, infection, in particular antimicrobial silver species, to some of such compounds, to medical devices comprising these compounds or compositions, to processes for the provision of such compounds, compositions and devices, and to a method for the treatment or prophylaxis of microbial, including bacterial, infections using such compounds, compositions or devices.

The clinical antimicrobial activity and efficacy of silver compounds is well known. These include, e.g. silver(I) nitrate and silver(I) sulphadiazine The in vitro antimicrobial efficacy of silver oxides has recently attracted commercial interest, as their efficacy can exceed that of traditional silver(I) compounds, and probably results from the presence of oxidation states of silver >1, and silver compounds of average silver oxidation state >1 have been patented for medical applications.

A significant impediment to the exploitation of silver-based antimicrobial therapies in medicine is their poor shelf-life stability and radiation sensitivity.

For example, the +1 oxidation state of silver, while an effective antimicrobial species, is particularly photo-sensitive. Exposure to electromagnetic radiation results in discolouration due to reduction to silver metal.

Further, the combination of silver compounds (including silver halides, silver nitrate, silver carbonate or silver oxides) with medical devices incorporating good donor ligand species (e.g. those comprising sulphur, nitrogen or oxygen atoms) can lead to severe stability problems, including loss of antimicrobial, including antibacterial, activity (due to reduction to silver metal) or discolouration (due to reduction by photographic means). These problems are particularly relevant to the nitrogen-rich polyurethanes on which a significant number of medical-grade materials, including foams, are based.

Compounds of silver(III) stable at room temperature and pressure are relatively rare. One such stable compound is ethylenebis(biguanidinium)-silver(III) sulphate. Such complexes of silver(III) known in the prior art are not formed from biologically acceptable species.

Further, although silver oxides are good examples of highly antimicrobial, including antibacterial, silver compounds, they are poorly compatible with most medical device substrate materials due to their strongly oxidising nature. Polyurethanes in combination with silver oxides results in a silver 'bleeding' process that unevenly discolours the device from shades ranging from yellow to brown. The combination of sugar or polysaccharide-based materials, including hydrogels based on carboxymethylcellulose, results in a similar, highly coloured effect being observed.

Biguanides are cationic compounds, which demonstrate good antimicrobial, including antibacterial, activity by microbial membrane disruption. A commercially successful manifestation of this property is embodied by poly(hexamethylenebiguanide) (PHMB), a polymeric biguanide, used to treat water facilities such as swimming pools. The silver(I) complex of PHMB is known (see U.S. Pat. No. 6,264,936).

An object of this invention is thus the provision of compositions comprising high oxidation state metal compounds, in particular silver(III) compounds, for the treatment or prophylaxis of microbial, including bacterial, infections, such compositions being stable at room temperature and pressure, compatible with medical device substrate materials, such as polyurethanes, notwithstanding their strongly oxidising properties, and containing no biologically unacceptable moieties, and medical devices incorporating these compounds or compositions.

Another object of this invention is the provision of some of such compounds for use in such compositions or devices.

A further object of this invention is the provision of a method for the treatment or prophylaxis of microbial, including bacterial, infections using such compounds, compositions or devices.

According to a first aspect of the present invention, there is provided a compound comprising a metal species and a biologically acceptable ligand, wherein the biologically acceptable ligand comprises a biguanide moiety, and wherein the biologically acceptable ligand forms a complex with the metal species in which the metal species is stabilised in an oxidation state greater than 1+.

According to a second aspect of the present invention, there is provided a compound for use as a medicament, the compound comprising a metal species and a biologically acceptable ligand, wherein the biologically acceptable ligand comprises a biguanide moiety, and wherein the biologically acceptable ligand forms a complex with the metal species in which the metal species is stabilised in an oxidation state greater than 1+.

According to a third aspect of the present invention, there is provided a compound for use in the treatment or prophylaxis of microbial, including bacterial, infections, comprising a metal species and a biologically acceptable ligand, wherein the biologically acceptable ligand comprises a biguanide moiety, and wherein the biologically acceptable ligand forms a complex with the metal species in which the metal species is stabilised in an oxidation state greater than 1+.

The metal species may be a Group IA or IB metal.

The metal species may be selected from the group consisting of silver, copper, gold, and zinc.

The metal species may be selected from the group consisting of silver (III), copper (III), gold (III), and zinc (IV).

According to a fourth aspect of the present invention, there is provided a composition comprising a compound according to the first, second, or third aspects of the present invention.

According to a fifth aspect of the present invention, there is provided a medical composition comprising a compound of a Group IA or IB metal in a higher oxidation state for the treatment or prophylaxis of microbial, including bacterial, infections, characterised in that the metal atom or ion is complexed by at least one biologically acceptable ligand comprising a biguanide moiety.

On contact with moisture, for example on wound contact, the compounds or compositions according to the invention act as a source of the antimicrobial metal in a higher oxidation state to provide treatment or prophylaxis of microbial, including bacterial, infections.

When used herein the term 'higher oxidation state' means the following. As is well known to those skilled in the art, in general Group IA or IB metals can have several oxidation states, and when used herein the term 'higher oxidation state' means any oxidation state other than the lowest above 0 and encompasses silver species, such as silver(III); copper species, including copper(III); gold species, including gold (III); and zinc species, including zinc(IV). It therefore means oxidation states greater than 1+.

When used herein the term 'ligand comprising a biguanide moiety' means a compound of the formula (I), (II) or (III) below.

It thus includes compounds of formula (I):

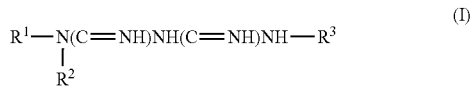

(I)

where $R^1$, $R^2$ and $R^3$ may be the same or different and are each H or an optionally substituted hydrocarbyl group, which may be aliphatic, araliphatic or aromatic, with the proviso that at least one of $R^1$, $R^2$ and $R^3$ is an optionally substituted hydrocarbyl group.

Examples of suitable $R^1$, $R^2$ and $R^3$ optionally substituted hydrocarbyl groups include straight- and branched-chain aliphatic hydrocarbyl groups, such as $C_{1-6}$ alkyl, e.g. methyl, $C_{5-8}$ cycloalkyl, e.g. cyclohexyl;

araliphatic hydrocarbyl groups including heteroaraliphatic hydrocarbyl groups, optionally substituted in the aryl group, such as phenyl straight- and branched-chain $C_{1-6}$ alkyl, e.g. phenethyl, optionally substituted in the phenyl group by halo, e.g. chloro or fluoro, $C_{1-6}$ alkyl, e.g. methyl, optionally substituted by halo, e.g. chloro or fluoro, e.g. trifluoromethyl, $C_{5-8}$ cycloalkyl, e.g. cyclohexyl, $C_{1-6}$ alkoxyl, e.g. methoxyl and ethoxyl, optionally substituted by halo, e.g. chloro or fluoro, e.g. trifluoromethoxyl, $C_{5-8}$ cycloalkyl, e.g. cyclohexyl, and/or nitro; and optionally substituted aromatic hydrocarbyl groups, including heteroaromatic hydrocarbyl groups, e.g. phenyl, optionally substituted in the phenyl group by halo, such as chloro or fluoro, $C_{1-6}$ alkyl, e.g. methyl, optionally substituted by halo, e.g. chloro or fluoro, e.g. trifluoromethyl, $C_{1-6}$ alkoxyl, e.g. methoxyl or ethoxyl, optionally substituted by halo, e.g. chloro or fluoro, e.g. trifluoromethoxyl, and/or $C_{5-8}$ cycloalkyl, e.g. cyclohexyl; and/or nitro.

Examples of suitable biologically acceptable biguanide ligands thus include 1,1-dimethylbiguanide (metformin), N-butylbiguanide (buformin), N-cyclohexylbiguanide;

N-(1-phenethyl)biguanide (phenformin),
1-(2,3-dichlorophenyl)biguanide, 1-(2-4-dichlorophenyl)biguanide, 1-(2,4-di-fluorophenyl)biguanide, 1-(2,5-dichlorophenyl)biguanide, 1-(2,5-difluoro-phenyl)biguanide, 1-(2,6-dichlorophenyl)biguanide, 1-(2-chlorophenyl)-biguanide, 1-(2-fluorophenyl)biguanide, 1-(3,4-dichlorophenyl)biguanide, 1-(3,5-dichlorophenyl)biguanide, 1-(3-chloro-4-fluorophenyl)-biguanide, 1-(3-chlorophenyl)biguanide, 1-(3-fluorophenyl)biguanide, 1-(4-chloro-phenyl)biguanide, 1-(4-chlorophenyl)biguanide, 1-(4-fluorophenyl)-biguanide, 1-(4-1-phenylbiguanide, tolylbiguanide, 1-(o-tolyl)-biguanide, 1-[3,5-di(trifluoromethyl)phenyl]biguanide, 1-[4-(trifluoromethyl)phenyl]-biguanide, N1-(4-ethoxyphenyl)biguanide, 1-[4-(trifluoromethoxy)phenyl]-biguanide, and nitrophenyl)biguanide.

It also includes compounds of formula (II):

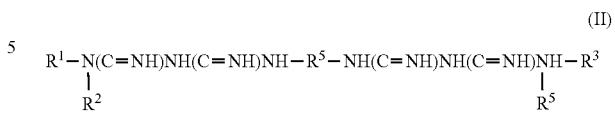

(II)

where
$R^1$, $R^2$, $R^3$ and $R^4$ may be the same or different and are each H or an optionally substituted hydrocarbyl group, which may be aliphatic, araliphatic or aromatic, with the proviso that at least one of $R^3$ and $R^4$ is an optionally substituted hydrocarbyl group, and
$R^5$ is an optionally substituted hydrocarbadiyl group, which may be aliphatic, araliphatic or aromatic.

Examples of suitable $R^1$, $R^2$, $R^3$ and $R^4$ optionally substituted hydrocarbyl groups include those so described for $R^1$, $R^2$ and $R^3$ under formula (I).

Examples of suitable $R^5$ optionally substituted hydrocarbadiyl groups include straight- and branched-chain aliphatic hydrocarbadiyl groups, such as $C_{1-20}$ alkylene, such as $C_{3-9}$ alkylene, e.g. methylene and hexamethylene, $C_{5-8}$ cycloalkadiyl e.g. cyclohexa-1,4-diyl;

araliphatic hydrocarbadiyl groups including heteroaraliphatic hydrocarbadiyl groups, optionally substituted in the arylene group, such as phenylene $C_{1-6}$ straight- and branched-chain alkylene, e.g. 1,4-phenyleneethandi-1,2-yl or 1,4-dimethandiylbenzene, optionally substituted in the phenylene group by halo, e.g. chloro or fluoro, $C_{1-6}$ alkyl, e.g. methyl, optionally substituted by halo, e.g. chloro or fluoro, e.g. trifluoromethyl, $C_{5-8}$ cycloalkyl, e.g. cyclohexyl, $C_{1-6}$ alkoxyl, e.g. methoxyl and ethoxyl, optionally substituted by halo, e.g. chloro or fluoro, e.g. trifluoromethoxyl, $C_{5-8}$ cycloalkyl, e.g. cyclohexyl, and/or nitro; and optionally substituted aromatic hydrocarbadiyl groups, including heteroaromatic hydrocarbadiyl groups, e.g. phenylene, optionally substituted in the phenylene group by halo, such as chloro or fluoro, $C_{1-6}$ alkyl, e.g. methyl, optionally substituted by halo, e.g. chloro or fluoro, e.g. trifluoromethyl, $C_{1-6}$ alkoxyl, e.g. methoxyl or ethoxyl, optionally substituted by halo, e.g. chloro or fluoro, e.g. trifluoromethoxyl, and/or $C_{5-8}$ cycloalkyl, e.g. cyclohexyl; and/or nitro.

Preferably, $R^5$ is of the formula: $(CH_2)_m$ where m is an integer in the range 3-20, more preferably an integer in the range 3-9.

Examples of suitable biologically acceptable biguanide ligands thus include chlorhexidine (1,1'-hexamethylenebis[5-(p-chlorophenyl)biguanide].

It also includes polymeric compounds of formula (III):

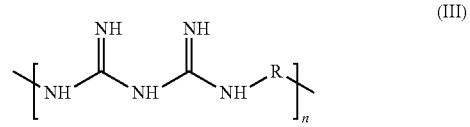

(III)

where R is an optionally substituted hydrocarbadiyl group, which may be aliphatic, araliphatic or aromatic.

Examples of suitable R optionally substituted hydrocarbadiyl groups include straight- and branched-chain aliphatic hydrocarbadiyl groups, such as $C_{1-20}$ alkylene, such as $C_{3-9}$ alkylene, e.g. methylene and hexamethylene, $C_{5-8}$ cycloalkadiyl e.g. cyclohexa-1,4-diyl;

Preferably, R is of the formula: $(CH_2)_m$ where m is an integer in the range 3-20, more preferably an integer in the range 3-9.

Examples of suitable biologically acceptable biguanide ligands thus include poly[(hexamethylene)biguanide].

The most preferable biguanides are those cleared for medical use including poly(hexamethylenebiguanide), chlorhexidine (1,1'-hexamethylenebis[5-(p-chlorophenyl)biguanide], metformin (N',N' dimethylbiguanide), phenformin (phenethylbiguanide) and buformin (N-butylbiguanide).

The water solubility of the so formed biguanide complexes can be tailored by the choice of suitable hydrophilic or hydrophobic biguanide ligands. Preferably, the biguanide complex is significantly insoluble in aqueous fluids including bodily fluids including wound exudate, serum, plasma and whole blood.

Preferably, the biguanide complex is coloured and dissociation of metal ions from the complex results in loss of colour intensity compared to the initial complex (biguanides are generally colourless). This offers a method of indicating capacity remaining.

In a sixth aspect the present invention provides a compound of a Group IA or IB metal in a higher oxidation state for the treatment or prophylaxis of microbial, including bacterial, infections, characterised in that the metal atom or ion is complexed by at least one a biologically acceptable ligand comprising a biguanide moiety, excluding ethylenebis-(biguanidinium)silver(II) sulphate.

A group of compounds of the sixth aspect of the present invention includes a compound of a Group IA or IB metal in a higher oxidation state for the treatment or prophylaxis of microbial, including bacterial, infections, characterised in that the metal atom or ion is complexed by at least one biologically acceptable ligand comprising a biguanide moiety of formula (I) as hereinbefore defined.

Examples of suitable and preferred $R^1$, $R^2$ and $R^3$ optionally substituted hydrocarbyl groups and biologically acceptable biguanide ligands include those so described under formula (I).

Another group of compounds of the sixth aspect of the present invention includes a compound of a Group IA or IB metal in a higher oxidation state for the treatment or prophylaxis of microbial, including bacterial, infections, characterised in that the metal atom or ion is complexed by at least one a biologically acceptable ligand comprising a biguanide moiety of formula (II) as hereinbefore defined, in which when $R^5$ is an optionally substituted straight- or branched-chain aliphatic hydrocarbadiyl group, it is $C_{3-20}$ alkylene, such as $C_{3-9}$ alkylene, e.g. methylene and hexamethylene, or $C_{5-8}$ cycloalkadiyl e.g. cyclohexa-1,4-diyl;

Examples of suitable and preferred $R^1$, $R^2$, $R^3$ and $R^4$ optionally substituted hydrocarbyl groups, and $R^5$ optionally substituted hydrocarbadiyl groups, and biologically acceptable biguanide ligands include those so described under formula (II).

A further group of compounds of the sixth aspect of the present invention includes a compound of a Group IA or IB metal in a higher oxidation state for the treatment or prophylaxis of microbial, including bacterial, infections, characterised in that the metal atom or ion is complexed by at least one biologically acceptable ligand comprising a biguanide moiety of formula (III) as hereinbefore defined.

Examples of suitable and preferred optionally substituted hydrocarbadiyl groups, and biologically acceptable biguanide ligands include those so described under formula (III).

A further group of compounds of the sixth aspect of the present invention includes a compound of a Group IA or IB metal in a higher oxidation state for the treatment or prophylaxis of microbial, including bacterial, infections, characterised in that the metal atom or ion is complexed by at least one biologically acceptable ligand comprising a biguanide moiety poly(hexamethylenebiguanide), chlorhexidine (1,1'-hexamethylenebis[5-(p-chlorophenyl)biguanide], o-tolylbiguanide and N',N'-dimethylbiguanide.

A group of such compounds includes a compound of silver(III), characterised in that the metal atom or ion is complexed by at least one biologically acceptable ligand comprising a biguanide moiety selected from poly(hexamethylenebiguanide), chlorhexidine (1,1'-hexamethylenebis[5-(p-chlorophenyl)biguanide], o-tolylbiguanide and N',N'-dimethylbiguanide.

Such antimicrobial, including antibacterial, compounds are compatible with most medical device substrate materials in spite of their strongly oxidising nature, even in combination with polyurethanes or sugar or polysaccharide-based materials, including hydrogels based on carboxymethylcellulose.

The antimicrobial efficacy of such silver compounds on a molar basis exceeds that of traditional silver(I) compounds in which the silver ion is complexed.

The preparation of monomeric silver(III) biguanide compounds is well known to those skilled in the art. In general, a silver(I) salt (e.g. nitrate) is oxidised by an oxidising agent (e.g. sodium persulphate, potassium peroxodisulphate) in the presence of a biguanide ligand. The so-formed complexes can be isolated in a straightforward manner (e.g. by precipitation).

The preparation of the compounds of the sixth aspect of the present invention can be effected in a similar fashion, using at least one biologically acceptable biguanide ligand and a compound of a Group IA or IB metal in its lowest oxidation state. The biguanide is preferably soluble in a common solvent.

Where the Group IA or IB metal in a higher oxidation state is silver(III), silver(I) sources for complexation can be any known sources, including silver acetate, silver acetylacetonate, silver benzoate, silver bromide, silver carbonate, sliver chloride, silver citrate, silver cyanate, silver cyclohexanebutyrate, silver fluoride, silver iodide, silver lactate, silver methanesulfonate, silver nitrate, silver perchlorate, silver permanganate, silver phosphate, silver sulfadiazine, silver sulphate, silver tetrafluoroborate, silver thiocyanate, silver p-toluenesulfonate, silver trifluoroacetate and silver trifluoromethanesulphonate.

The silver source is preferably soluble in a common solvent.

Oxidising agents for the conversion of silver(I) to silver (III) can be any of those known including sodium persulphate and potassium peroxodisulphate.

The oxidising agent is preferably soluble in a common solvent.

Preferred combinations of biguanide, silver source and oxidising agent are those involving:

chlorhexidine (1,1'-hexamethylenebis[5-(p-chlorophenyl) biguanide], silver nitrate and sodium persulphate;

PHMB, silver nitrate and sodium persulphate; and o-tolylbiguanide, silver sulphate and sodium persulphate.

Preferred reaction solvents are ethyl alcohol, methyl alcohol and water or combinations of these solvents.

Preferred reaction systems include methanolic solutions of biguanide ligands with aqueous solutions of silver salts to form a silver(I) complex. An aqueous solution of oxidising agent is then added, resulting in the precipitation of the desired silver(III) complex.

According to a seventh aspect of the present invention, there is provided a medical device comprising a compound according to the first, second, third or sixth aspects of the present invention or a composition according to the fourth or fifth aspects of the present invention.

Suitable devices include dressings, including topical dressings for the management of wounds, including surgical, acute and chronic wounds, and burns; implants including artificial joints, such as artificial hips and artificial knees, organs and scaffolds for tissue repair and stents; and hospital equipment, such devices including, for example, operating tables.

Often the compound of the first, second, third, or sixth aspects of the present invention or a composition of the fourth or fifth aspects of the present invention is present as a coating on a surface of the medical device or a component thereof.

Suitable manufacturing methods are known to those in the art and include solvent dipping and powder coating. Preferably, the article to be treated is impregnated with a biguanide compound or biguanide polymer and oxidised in the presence of a silver salt, for example silver(I) nitrate or silver(I) sulphate. Alternatively, the silver(III) biguanide compound or polymer can be manufactured in bulk and applied to the article by physical means, including attachment via an adhesive or powder coating or blasting.

Articles so produced can be stored for long periods, up to several years, at ambient temperature and pressure in traditional sterile packaging.

According to an eighth aspect of the present invention, there is provided a method for the treatment or prophylaxis of microbial, including bacterial, infections, comprising the use of a compound according to the first, second, third, or sixth aspects of the present invention, a composition according to the fourth or fifth aspects of the present invention, or a medical device according to the seventh aspect of the present invention.

Such a method for the treatment or prophylaxis of microbial, including bacterial, infections is useful in particular for the management of wounds, including surgical, acute and chronic wounds, and burns.

The present invention is further illustrated by the following Examples.

EXAMPLE 1

Preparation of Silver(III) Chlorhexidine (1,1'-hexamethylenebis[5-(p-chlorophenyl)biguanide] Complex Chlorhexidine (1,1'-hexamethylenebis[5-(p-chlorophenyl)biguanide] (1.00 g) was dissolved in 100 ml warm methanol. To this stirred solution was added dropwise an aqueous solution of silver nitrate (0.34 g) made up in 5 ml distilled water. This was followed dropwise by an aqueous solution of sodium persulphate (0.94 g) made up in 5 ml distilled water. The reaction mixture was warmed until the orange-brown fully developed. The precipitate was Buchner filtered under vacuum, washed three times with warm methanol and stored at ambient temperature and pressure.

EXAMPLE 2

Preparation of Silver(III) PHMB Complex

PHMB (0.400 g) was dissolved in 50 ml methanol. To this stirred solution was added dropwise an aqueous solution of silver nitrate (0.185 g) made up in 2 ml distilled water. This was followed dropwise by an aqueous solution of sodium persulphate (0.520 g) made up in 2 ml distilled water.

The reaction mixture was stirred until the orange-brown fully developed.

The precipitate was Buchner filtered under vacuum, washed three times with warm methanol and stored at ambient temperature and pressure.

EXAMPLE 3

Preparation of Silver(III) o-tolybiguanide Complex o-tolylbiguanide (1.00 g) was dissolved in 50 ml methanol. To this stirred solution was added dropwise an aqueous solution of silver nitrate (0.44 g) made up in 5 ml distilled water. This was followed dropwise by an aqueous solution of sodium persulphate (1.25 g) made up in 5 ml distilled water.

The reaction mixture was stirred until the orange-brown fully developed.

The precipitate was Buchner filtered under vacuum, washed three times with warm methanol and stored at ambient temperature and pressure.

EXAMPLE 4

Preparation of a Silver(III) o-tolylbiguanide Complex-coated Material

A 5 $cm^2$ swatch of Profore WCL (Smith & Nephew Medical Ltd) was immersed in a methanolic solution of o-tolylbiguanide (50 mg/ml) for 5 seconds. The swatch was removed and warm air dried using a hot air gun. The swatch was dipped into an aqueous solution of silver nitrate (10 mg/ml) for 10 seconds, removed and rinsed with excess distilled water. The swatch was then dipped into a warmed aqueous solution of sodium persulphate (10 mg/ml) until the orange colour fully developed (approximately 15 seconds). The swatch was removed, rinsed in excess distilled water and air-dried for storage at ambient temperature and pressure.

EXAMPLE 5

Preparation of Silver(III) Chlorhexidine (1,1'-hexamethylenebis[5-(p-chlorophenyl)biguanide] Complex Formulated in IntraSite Gel 5 mg of silver(III) chlorhexidine complex (Example 1) was dispersed by mechanical mixing into 3 g IntraSite Gel (Smith & Nephew Medical Ltd). After 24 h standing, a stable, uniformly orange-coloured hydrogel was formed.

EXAMPLE 6

Preparation of Silver(III) PHMB Complex Formulated in IntraSite Gel 5 mg of silver(III) PHMB complex (Example 2) was dispersed by mechanical mixing into 3 g IntraSite Gel (Smith & Nephew Medical Ltd). After 24 h standing, a stable, uniformly orange-coloured hydrogel was formed.

EXAMPLE 7

Evaluation of Stability of IntraSite Gel-based Silver Formulations

The gel formulations prepared in Examples 5 and 6 were compared to alternative silver source formulations, similarly prepared (5 mg silver species per 3 g IntraSite Gel). Alternative silver sources were: silver nitrate, silver carbonate, silver chloride, silver bromide, silver iodide, silver(I) oxide ($Ag_2O$) and silver(I,III) oxide (AgO). Each formulation was placed into a sterile transparent plastic tube (Sterilin Ltd) for observation over 24 hours.

In every case excepting the silver(III) biguanides prepared in Examples 5 and 6 the formulations had severely discoloured to grey-black, with some multi-coloured discolouration surrounding the oxide particles of the silver oxide formulations.

Although this test was conducted for only 24 hours, the same phenomena can be observed, over a matter of days, weeks or months for other silver presentation system containing oxygen, nitrogen or sulphur ligand species or oxidisable substrates (e.g. sugars or polysaccharides).

EXAMPLE 8

Evaluation of Antimicrobial Activity of Silver(III) Biguanides Prepared in Examples 1-3

*Pseudomonas aeruginosa* NCIMB 8626 and *Staphylococcus aureus* NCTC 10788 were harvested. Serial 1:10 dilutions were performed to give a final concentration of $10^8$ bacteria/ml. Further dilutions were made for an inoculum count, down to $10^{-8}$ bacteria/ml, with the number of bacteria/ml determined using the pour plate method.

Two large assay plates were then set up and 140 ml of Mueller-Hinton agar was added evenly to the large assay plates and allowed to dry (15 minutes). A further 140 ml of agar was seeded with the corresponding test organism and poured over the previous agar layer. Once the agar had set (15 minutes), the plate was dried at 37° C. for 30 minutes with the lid removed. 8 mm plugs were removed from the plate by biopsy punch.

In triplicate, 10 mg of the compounds prepared in Examples 1-3 were placed onto each plug hole followed by 200 ul sterile water. The plates were then sealed and incubated at 37° C. for 24 hours. The size of the microbial, including bacterial, zone cleared was measured using a Vernier calliper gauge, triplicates were averaged:

| Organism | Compound | Zone of Inhibition/mm |
|---|---|---|
| Staphylococcus aureus NCTC 10788 | Example 1 | 6.4 |
| Staphlyococcus aureus NCTC 10788 | Example 2 | 14.3 |
| Staphlyococcus aureus NCTC 10788 | Example 3 | 8.4 |
| Pseudomonas aeruginosa NCIMB 8626 | Example 1 | 5.4 |

-continued

| Organism | Compound | Zone of Inhibition/mm |
|---|---|---|
| Pseudomonas aeruginosa NCIMB 8626 | Example 2 | 9.5 |
| Pseudomonas aeruginosa NCIMB 8626 | Example 3 | 7.4 |

Thus, Examples 1-3 exhibit significant antimicrobial behaviour.

The invention claimed is:

1. A method for the treatment of microbial infections, comprising administering to an individual a compound comprising a metal species and a biologically acceptable ligand, wherein the metal species is selected from the group consisting of silver (III), copper (III), and gold (III); wherein the biologically acceptable ligand comprises a biguanide moiety; wherein the biologically acceptable ligand forms a complex in which the metal species is stabilized in an oxidation state greater than 1+; and wherein the step of administering to an individual comprises contacting the individual with the compound.

2. The method of claim 1, wherein contacting the individual with the compound comprises contacting the individual with a medical device comprising the compound.

3. The method of claim 1, wherein the biologically acceptable ligand has the formula:

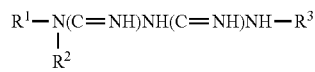

wherein $R^1$, $R^2$, and $R^3$ are independently H or a hydrocarbyl group.

4. The method of claim 1, wherein the biologically acceptable ligand has the formula:

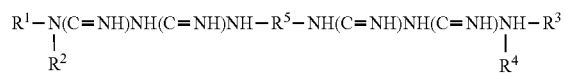

wherein $R^1$, $R^2$, $R^3$, and $R^4$ are independently H or a hydrocarbyl group and $R^5$ is a hydrocarbadiyl group.

5. The method of claim 1, wherein the biologically acceptable ligand has the formula:

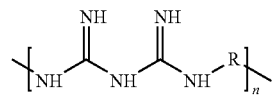

wherein R is a hydrocarbadiyl group and n is 1 or more.

6. The method of claim 1, wherein the biologically acceptable ligand is selected from the group consisting of poly(hexamethylenebiguanide), chlorhexidine (1,1'-hexamethylenebis[5-(p-chlorophenyl)biguanide], metformin (N', N'dimethylbiguanide), phenformin (phenethylbiguanide) and buformin (N-butylbiguanide).

7. The method of claim 2, wherein the medical device comprises a wound or burn dressing, an implant, a scaffold for tissue repair, or a stent.

* * * * *